(12) United States Patent
Heacock et al.

(10) Patent No.: US 8,859,621 B2
(45) Date of Patent: *Oct. 14, 2014

(54) PHARMACEUTICAL FORMULATIONS OF MODAFINIL

(75) Inventors: Craig S. Heacock, Downingtown, PA (US); Alpa B. Parikh, Avondale, PA (US); Piyush R. Patel, Wallingford, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/590,912

(22) Filed: Aug. 21, 2012

(65) Prior Publication Data

US 2012/0316244 A1 Dec. 13, 2012

Related U.S. Application Data

(63) Continuation of application No. 12/150,056, filed on Apr. 24, 2008, now Pat. No. 8,268,892, which is a continuation of application No. 10/660,058, filed on Sep. 11, 2003, now abandoned.

(60) Provisional application No. 60/410,395, filed on Sep. 13, 2002.

(51) Int. Cl.
*A61K 31/165* (2006.01)
*A61K 9/20* (2006.01)

(52) U.S. Cl.
CPC ............ *A61K 9/2018* (2013.01); *A61K 9/2054* (2013.01); *A61K 9/2027* (2013.01); *A61K 31/165* (2013.01)
USPC ........................................................ 514/618

(58) Field of Classification Search
CPC ................................................. A61K 31/165
USPC ........................................................ 514/618
See application file for complete search history.

(56) References Cited

U.S. PATENT DOCUMENTS

| | | |
|---|---|---|
| 1,570,994 A | 1/1926 | Cook |
| 3,629,393 A | 12/1971 | Nakamoto et al. |
| 4,177,290 A | 12/1979 | Lafon |
| 4,299,834 A | 11/1981 | Austel et al. |
| 4,431,645 A | 2/1984 | Smith et al. |
| 4,584,285 A | 4/1986 | Doll et al. |
| 4,710,519 A | 12/1987 | Finnan et al. |
| 4,748,023 A | 5/1988 | Tamas et al. |
| 4,927,855 A * | 5/1990 | Lafon ........................ 514/618 |
| 5,084,277 A | 1/1992 | Greco et al. |
| 5,180,745 A | 1/1993 | Lafon |
| 5,391,576 A | 2/1995 | Lafon |
| 5,401,776 A | 3/1995 | Laurent |
| 5,456,920 A | 10/1995 | Matoba et al. |
| 5,506,248 A | 4/1996 | Nikfar et al. |
| 5,569,654 A | 10/1996 | Armour et al. |
| 5,612,379 A | 3/1997 | Laurent |
| 5,618,845 A | 4/1997 | Grebow et al. |
| 5,719,168 A | 2/1998 | Laurent |
| 5,843,347 A | 12/1998 | Nguyen |
| 5,948,437 A | 9/1999 | Parikh et al. |
| 6,042,847 A | 3/2000 | Kerc et al. |
| 6,143,323 A | 11/2000 | Yabuki et al. |
| 6,204,245 B1 | 3/2001 | Siegel et al. |
| 6,248,363 B1 | 6/2001 | Patel et al. |
| 6,267,985 B1 | 7/2001 | Chen et al. |
| 6,294,192 B1 | 9/2001 | Patel et al. |
| RE37,516 E | 1/2002 | Grebow et al. |
| 6,337,327 B1 | 1/2002 | Tuffin et al. |
| 6,346,548 B1 * | 2/2002 | Miller et al. ................. 514/618 |
| 6,451,339 B2 | 9/2002 | Patel et al. |
| 6,455,588 B1 | 9/2002 | Scammell |
| 6,462,089 B1 | 10/2002 | Battaglia et al. |
| 6,488,164 B2 | 12/2002 | Miller et al. |
| 6,489,363 B2 | 12/2002 | Jacobs et al. |
| 6,492,396 B2 | 12/2002 | Bacon et al. |
| 6,569,463 B2 | 5/2003 | Patel et al. |
| 6,670,358 B2 | 12/2003 | Bacon et al. |
| 6,919,378 B2 | 7/2005 | Jacobs et al. |
| 7,229,644 B2 | 6/2007 | Corvari et al. |
| 7,297,346 B2 | 11/2007 | Corvari et al. |
| 8,268,892 B2 * | 9/2012 | Heacock et al. .............. 514/618 |
| 2001/0034373 A1 | 10/2001 | Miller et al. |
| 2002/0098240 A1 | 7/2002 | Jacobs et al. |
| 2002/0160982 A1 | 10/2002 | Jacobs et al. |
| 2003/0022940 A1 | 1/2003 | Corvari et al. |
| 2003/0077297 A1 | 4/2003 | Chen et al. |
| 2003/0104048 A1 | 6/2003 | Patel et al. |
| 2003/0125391 A1 | 7/2003 | Jacobs et al. |

(Continued)

FOREIGN PATENT DOCUMENTS

| | | |
|---|---|---|
| FR | 2702968 | 9/1994 |
| WO | WO 94/21371 | 9/1994 |

(Continued)

OTHER PUBLICATIONS

T.A. Rugino et al. Effects of Modafinil in Children with attention Deficit/Hyperactivity Disorder: An Open Label Study, J. Am. Acad. Chil adolesc. Psychiatry, 40:2, Feb. 2001.*

(Continued)

*Primary Examiner* — Jennifer M Kim

(57) ABSTRACT

Compositions of modafinil and methods of treating neurologically related conditions with the administration of modafinil. Also compositions that include modafinil and one or more excipients such as diluents, disintegrants, binders and lubricants.

10 Claims, 5 Drawing Sheets

(56) References Cited

U.S. PATENT DOCUMENTS

| | | | |
|---|---|---|---|
| 2003/0171439 A1* | 9/2003 | Lawyer et al. | 514/618 |
| 2003/0220403 A1 | 11/2003 | Corvari et al. | |
| 2004/0116532 A1 | 6/2004 | Heacock et al. | |

FOREIGN PATENT DOCUMENTS

| | | |
|---|---|---|
| WO | WO 99/12524 | 3/1999 |
| WO | WO 00/37055 | 6/2000 |
| WO | WO 01/13906 | 3/2001 |
| WO | WO01/13906 A2 * | 3/2001 |
| WO | WO 02/30414 | 4/2002 |
| WO | WO 02/096401 | 12/2002 |
| WO | WO 03/068186 | 8/2003 |
| WO | WO 2004/004692 | 1/2004 |
| WO | WO 2004/010979 | 2/2004 |

OTHER PUBLICATIONS

Ballas et al. Expert REv. Neurotherapeutics, 2002, 2(4), pp. 449-457.*
U.S. Appl. No. 11/550,588, Heacock et. al., pending.
U.S. Appl. No. 11/981,048, Heacock et al., pending.
U.S. Appl. No. 12/696,538, Corvari et al., pending.
Wong Y.N. et al, *J. Clin. Pharmacol*,1999, 39:30-40.
Rugino T.A. and Copley T.C., *J. Am. Acad. Child Adolesc. Psychiatry*, 2001, 40:2, 230-235.
J.M. Swanson et al., *Modafinil in Children with ADHD: A Randomized, Placebo-Controlled Study*, No. 44, American Psychiatric Assoc., 156th Annual Mtg., San Francisco, CA, May 2003.
Biederman, J. et al., *Modafinil Improves ADHD Symptoms in Children in a Randomized, Double-Blind, Placebo-Controlled Study*, No. 36, American Psychiatric Assoc., 156th Annual Mtg., San Francisco, CA, May 2003.
Biederman, J. et al., *Modafinil Improves ADHD Symptoms in Children*, Proc. 43rd New Clinical Drug Evaluation Unit Mtg., Boca Raton, FL, Poster Session 11-53, May 2003.
Rugino, T.A. et al., *Effects of Modafinil in Children With Attention-Deficit/Hyperactivity Disorder: An Open Label Study*, J. Am. Acad. Child Adolesc. Psychiatry, 40:2, Feb. 2001.
Gunsel, WC et al., "Tablets. In *The Theory and Practice of Industrial Pharmacy*; Leon Lachman, Herbert A. Lieberman, Joseph L. Kanig, Eds.; Henry Kimpton Publishers", Great Britain, 1976, 321-358.
Deak, D. et al., "Use of different cellulose derivatives for the preparation of tablets with a high active agent content", *S.T.P. Pharma Sciences* 1999, 9(6), 525-529.
Cephalon, "Provigil® (modafinil) Tablets", FDA Approved Labeling Dec. 1998.
Edgar et al., "Modafinil Induces Wakefulness Without Intensifying Motor Activity or Subsequent Rebound Hypersomnolence in the Rat," Journal of Pharmacology and ExperimentalTherapeutics, (1997), vol. 283, No. 2, pp. 757-769.
Rudnic et al., "Oral Solid Dosage Forms," Gennaro publisher, Remington: The Science and Practice of Pharmacy, (1995), Mack Publishing Company, Easton, PA, pp. 1615-1620.
Hermant et al., "Awakening properties of modafinil: effect on nocturnal activity in monkeys (*Macaca mulatta*) after acute and repeated administration," Psychopharmacology, (1991), 103(1), pp. 28-32.
Kibbe, Handbook of Pharmaceutical Excipients, 3rd Ed., 2000, American Pharmaceutical Association, Pharmaceutical Press, Washington, DC, Sec. 7, pp. 87, 102, 276, 305, 433, 528.
Lin et al., "Role of catecholamines in the modafinil and amphetamine induced wakefulness, a comparative pharmacological study in the cat," Brain Research, (1992), 591, pp. 319-326.
Panckeri et al., "Modafinil Decreases Hypersomnolence in the English Bulldog, a Natural Animal Model of Sleep-Disordered Breathing," Sleep, (1996), 19(8), pp. 626-631.
Shelton et al., "Comparative Effects of Modafinil and Amphetamine on Daytime Sleepiness and Cataplexy of Narcoleptic Dogs," Sleep, (1995), 18(10), pp. 817-826.
Taylor et al., "Efficacy of Modafinil Compared to Dextroamphetamine for the Treatment of Attention Deficit Hyperactivity Disorder in Adults," Journal of Child and Adolescent Psychopharmacology, (2000), vol. 10(4), pp. 311-320.
Touret et al., "Awakening properties of modafinil without paradoxical sleep rebound: comparative study with amphetamine in the rat," Neuroscience Letters, (1995), vol. 189, pp. 43-46.
Complaint for Declaratory Relief that US Patent No. 7,297,346 is invalid or not infringed, *Apotex, Inc. v. Cephalon, Inc*, filed May 27, 2009 in the U.S. District Court for the Eastern District of Pennsylvania.
Paragraph IV Certification Notice Letter for U.S. Patent No. 7,297,346 dated Feb. 16, 2009.
United States Pharmacopeia, Povidone Monograph, (2011).
European Pharmacopeia, Povidone Monograph, (2005).
Plasdone® Povidone Product Guide, ISP Pharmaceuticals, (2007).
Ballas et al., Expert Rev. Neurotherapeutics (2002), 2(4), pp. 449-457.
STN database Registry file; 9003-39-8/RN Nov. 16, 1984.
Broughton, R.J. et al., "Randomized, double-blind, placebo-controlled crossover trial of modafinil in the treatment of excessive daytime sleepiness in narcolepsy," *Neurology*, 1997, 49, 444-451.
Biederman et al., "A Comparison of Once-Daily and Divided Doses of Modafinil in Children With Attention-Deficit/Hyperactivity Disorder: A Randomized, Double-Blind, and Placebo-Controlled Study", *J. Clin. Psychiatry*, 2006, 67, 727-735.

* cited by examiner

PHARMACEUTICAL FORMULATIONS OF MODAFINIL

This application is a continuation of application Ser. No. 12/150,056, filed Apr. 24, 2008, which is a continuation of application Ser. No. 10/660,058, filed Sep. 11, 2003, which claims the benefit of provisional Application No. 60/410,395, filed Sep. 13, 2002.

FIELD OF THE INVENTION

The present invention is related to compositions of modafinil and methods of treating neurologically related conditions with the administration of modafinil. The present invention also relates to compositions that include modafinil and one or more excipients such as diluents, disintegrants, binders and lubricants.

BACKGROUND OF THE INVENTION

Modafinil, $C_{15}H_{15}NO_2S$, also known as 2-(benzhydrylsulfinyl) acetamide, or 2-[(diphenylmethyl) sulfinyl]acetamide, is a synthetic acetamide derivative with wake-promoting activity, the structure of which has been described in French Patent No. 78 05 510 and in U.S. Pat. No. 4,177,290 ('290), and which has been approved by the United States Food and Drug Administration for use in the treatment of excessive daytime sleepiness associated with narcolepsy. Modafinil has been tested for treatment of several behavioral conditions in combination with various agents including apomorphine, amphetamine, reserpine, oxotremorine, hypnotics, yohimbine, 5-hydroxytryptophan, and monoamine oxidase inhibitors, as described in the cited patents. A method of preparation of a racemic mixture is described in the '290 patent and a method of preparation of a levorotatory isomer is described in U.S. Pat. No. 4,927,855 (both incorporated herein by reference). The levorotatory isomer is reported to be useful for treatment of hypersomnia, depression, Alzheimer's disease and to have activity towards the symptoms of dementia and loss of memory, especially in the elderly. Modafinil has also been found to have application in the treatment of fatigue, and in particular the treatment of fatigue associated with multiple sclerosis, as well as sleepiness, Parkinson's disease, cerebral ischemia, stroke, sleep apneas, eating disorders, attention deficit hyperactivity disorder (described further below), for stimulation of appetite or weight gain, for promotion of wakefulness, or for improvement of cognitive dysfunction.

The primary pharmacological activity of modafinil is to promote wakefulness. Modafinil promotes wakefulness in rats (Touret et al., 1995; Edgar and Seidel, 1997), cats (Lin et al., 1992), canines (Shelton et al, 1995) and non-human primates (Hernant et al, 1991) as well as in models mimicking clinical situations, such as sleep apnea (English bulldog sleep disordered breathing model) (Panckeri et al, 1996) and narcolepsy (narcoleptic canine) (Shelton et al, 1995).

Modafinil has also been described as an agent with activity in the central nervous system, and as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas and disorders of central origin (U.S. Pat. No. 5,612,379). U.S. Pat. No. 5,618,845 describes modafinil preparations of a defined particle size less than about 200 microns. In addition, modafinil may be used in the treatment of eating disorders, or to promote weight gain or stimulate appetite in humans or animals (U.S. Provisional Patent Application No. 60/150,071, incorporated herein by reference), or in the treatment of attention deficit hyperactivity disorder (ADHD) as described in U.S. Pat. No. 6,346,548, or fatigue, especially fatigue associated with multiple sclerosis (U.S. Provisional Patent Application No. 60/149,612, incorporated herein by reference). ADHD is a chronic neuropsychiatric disorder in children that is characterized by developmentally inappropriate hyperactivity, impulsivity, and inattention. ADHD is estimated to affect 3%-5% of school-age children. The core ADHD symptoms in adults include a frequent and persistent pattern of inattention/distractibility and/or hyperactivity-impulsivity. The most common symptoms exhibited in ADHD adults are marked inattention, poor concentration, easy distractibility, day dreaming, forgetfulness, and a frequent shift in activities. ADHD adults also report marked impulsivity, intrusiveness, low frustration/stress tolerance, temper tantrums, irritability, and extreme impatience. Less commonly reported symptoms in adults include hyperactivity, which may be confined to fidgeting, or an inward feeling of jitteriness or restlessness. In addition to the core ADHD symptoms, adults with ADHD often exhibit associated clinical characteristics such as boredom, social inappropriateness, and chronic conflicts in social situations.

Modafinil was known in the art in the form of a therapeutic package, marketed under the name Provigil®. Provigil® is a pharmaceutical product sold by Cephalon, Inc. of West Chester, Pa. Provigil® is supplied as tablets containing 100 mg or 200 mg modafinil, with several excipients, including magnesium silicate and talc. In commercial use, modafinil-containing therapeutic packages are labeled for use in treating excessive daytime sleepiness associated with narcolepsy.

SUMMARY OF THE INVENTION

The present invention is directed to a pharmaceutical composition containing about 250 to about 350 mg of modafinil.

The present invention is also directed to a pharmaceutical composition containing about 250 to about 450 mg of modafinil.

The present invention is also directed to methods of treating attention deficit hyperactivity disorder and attention deficit disorder by administering between about 250 to about 350 mg of modafinil to a subject.

The present invention is also directed to methods of treating attention deficit hyperactivity disorder and attention deficit disorder by administering between about 250 to about 450 mg of modafinil to a subject.

The present invention is also directed to a unit dose of modafinil having a reduced overall unit dose size and/or volume while simultaneously having a higher percentage, by weight, of modafinil. The unit dose can be free of magnesium silicate or talc, and can contain about 250 to about 350 mg of modafinil, wherein about 70-90% of the total weight of the unit dose is modafinil.

The present invention is also directed to a unit dose of modafinil having a reduced overall unit dose size and/or volume while simultaneously having a higher percentage, by weight, of modafinil. The unit dose can be free of magnesium silicate or talc, and can contain about 250 to about 450 mg of modafinil, wherein about 70-90% of the total weight of the unit dose is modafinil.

DETAILED DESCRIPTION OF THE INVENTION

Figure 1:
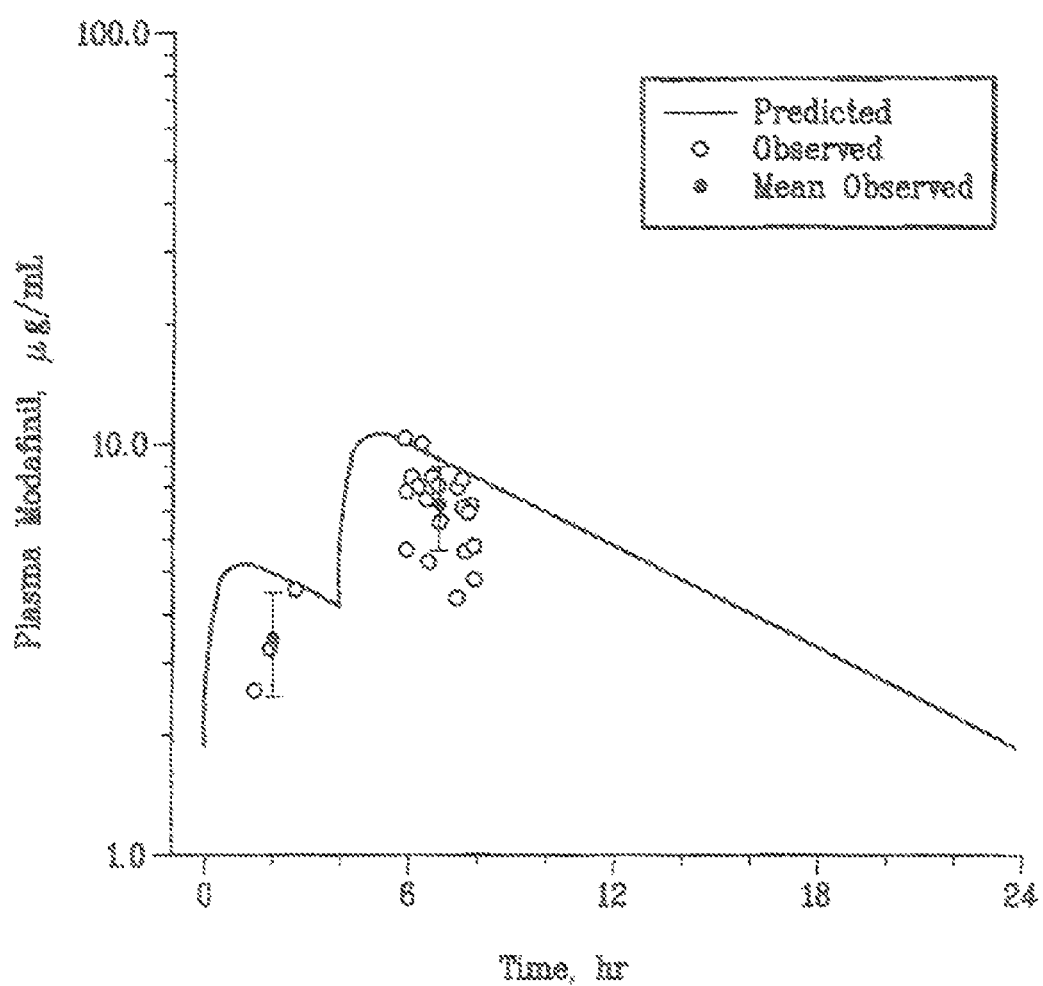
FIG. 1 represents a human blood plasma concentration curve of modafinil after an initial dose of 100 mg of modafinil followed 4 hours later by a 200 mg dose of modafinil.

As used herein, "about" refers to a range of values ±10% of a specified value. For example, "about 20" includes ±10% of 20, or from 18 to 22, inclusive.

As used herein, "modafinil" refers to modafinil, its racemic mixtures, individual isomers (for example, the (−) isomer or the "R" isomer of modafinil), acid addition salts, such as a metabolic acid of modafinil, benzhydrylsulfinylacetic acids, and its sulfone forms, hydroxylated forms, polymorphic forms, analogs, derivatives, cogeners and prodrugs thereof. Prodrugs are known in the art as compounds that are converted to the active agent (modafinil) in the body of a subject.

As used herein, the term "pharmaceutically acceptable" refers to those compounds, materials, compositions, and/or unit doses which are, within the scope of sound medical judgment, suitable for administration to human beings, e.g., without unacceptable toxicity, irritation, allergic response, or other problems or complications commensurate with a reasonable benefit/risk ratio.

A "pharmaceutical composition", as used herein, means a medicament for use in treating a mammal, e.g., a human, that comprises modafinil. A pharmaceutical composition according to the invention may also, but does not of necessity, include one or more non-toxic pharmaceutically acceptable carrier.

As used herein, "therapeutically effective amount" refers to an amount that is effective in reducing, eliminating, treating, preventing or controlling the symptoms of herein-described diseases and conditions.

Similarly, a "method of treating" is a method of reducing, eliminating, treating, preventing or controlling the symptoms of herein-described diseases and conditions. It is understood that the effect of pharmacological agents will vary among a large population of subjects.

As used herein, "pharmaceutical unit dose," "unit dose" or "unit dose form" means a single dose which is capable of being administered to a subject, and which can be readily handled and packaged, remaining as a physically and chemically stable unit dose comprising either modafinil, or a pharmaceutically acceptable composition comprising modafinil.

As used herein, "consisting essentially of" a specified amount of a pharmaceutically active agent means that there is no additional amount of that agent. The presence of other ingredients, e.g., excipients and/or lubricants, etc., is not precluded. The presence of additional other pharmaceutically active agents is also not precluded.

As used herein, "substantially" means approximating to a great extent or degree.

1. Amounts of Modafinil of the Present Invention

In one embodiment, a composition of the present invention includes a pharmaceutical composition of modafinil. The pharmaceutical composition can further include at least one pharmaceutical unit dose (hereafter "unit dose") of modafinil, typically in a solid unit dose form, such as a tablet or capsule. For the reasons set forth below, a composition of the present invention can include between about 250 to about 350 mg of modafinil or between about 250 to about 450 mg of modafinil. In other embodiments, a composition can include between about 275 to about 325 mg of modafinil or about 325 to about 425 mg of modafinil. In another embodiment, a composition can include about 255 mg of modafinil, about 300 mg of modafinil, about 340 mg of modafinil or about 425 mg of modafinil. In yet other embodiments, a composition of the invention can include about 250, 255, 260, 265, 270, 275, 280, 285, 290, 295, 300, 305, 310, 315, 320, 325, 330, 335, 340, 345, or 350 mg of modafinil, or about 355, 360, 365, 370, 375, 380, 385, 390, 395, 400, 405, 410, 415, 420, 425, 430, 435, 440, 445, or 450 mg of modafinil. Preferably, a unit dose can include about 255, 300, 340 or 425 mg of modafinil. Most preferably, a unit dose can include 355, 300, 340 or 425 mg of modafinil.

In yet another embodiment, a composition of the invention consists essentially of about 250 to about 350 mg of modafinil or about 250 to about 450 mg of modafinil. In another embodiment, a pharmaceutical composition of the invention consists essentially of about 275 to 325 mg of modafinil or about 325 to about 425 mg of modafinil. In yet another embodiment, a composition of the invention consists essentially of about 255 mg of modafinil, about 300 mg of modafinil, about 340 mg of modafinil or about 425 mg of modafinil, i.e., it does not contain more or less modafinil, but can contain other ingredients, e.g., excipients or other active agents. In yet another embodiment, a composition of the invention consists essentially of about 250, 255, 260, 265, 270, 275, 280, 285, 290, 295, 300, 305, 310, 315, 320, 325, 330, 335, 340, 345 or 350 mg of modafinil, or about 355, 360, 365, 370, 375, 380, 385, 390, 395, 400, 405, 410, 415, 420, 425, 430, 435, 440, 445, or 450 mg of modafinil. Preferably, a unit dose consists essentially of about 255, 300, 340 or 425 mg of modafinil. Most preferably, a unit dose consists essentially of 255, 300, 340 or 425 mg of modafinil.

A pharmaceutical composition of the invention can also be a liquid, softgel, suspension, emulsion, microemulsion, complex, as well as a solid solution form which can be dispensed in a manner that delivers a requisite amount of modafinil as set forth herein. A pharmaceutical composition of the present invention can also be a modified release form such as, but not limited to, a bi-modal or extended release form.

Conventional administrations of modafinil included discrete effective amounts of modafinil, typically either single 100 mg or 200 mg unit doses. To treat ADHD using these conventional unit doses in clinical studies, modafinil was administered as a 100 mg dose followed 4-6 hours later by a 200 mg dose, or alternatively, a 200 mg dose followed 4-6 hours later by a 100 mg dose. Such dosing regimens are referred to as a "split dose," and are particularly effective for treating ADHD and were considered necessary to prevent blood levels of modafinil from obtaining undesirable levels.

Figure 4:
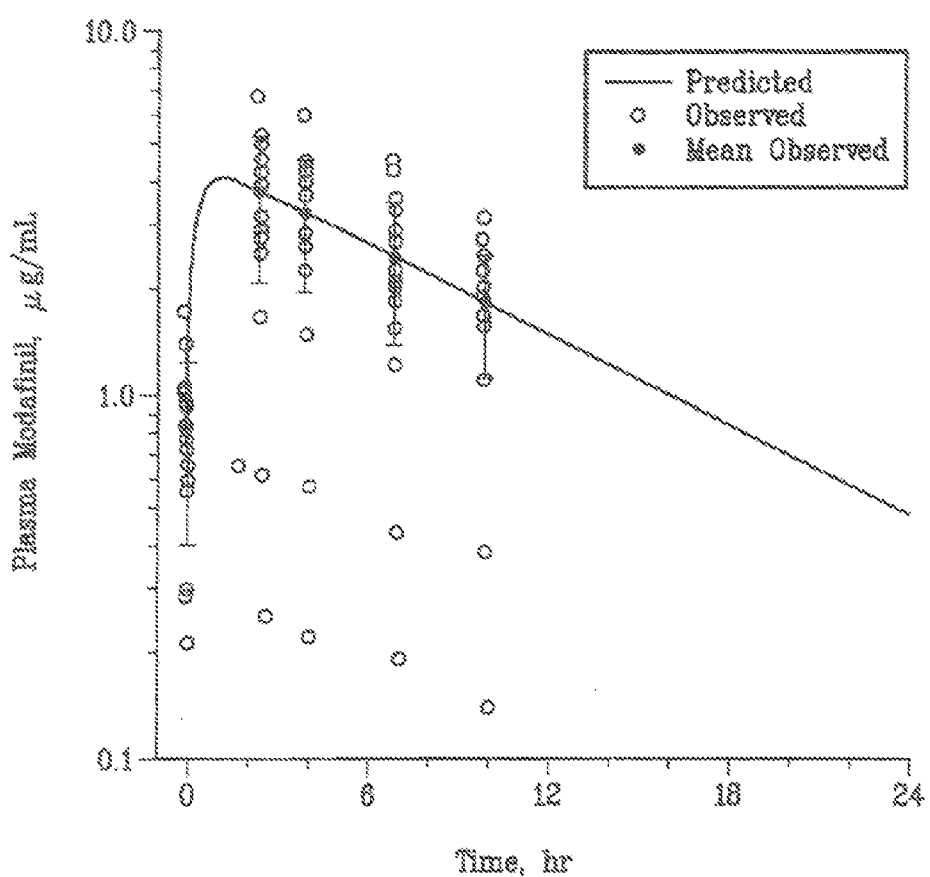
FIG. 4 represents a human blood plasma concentration curve of modafinil after a single dose of 100 mg of modafinil.

From previous 100 mg studies, generally summarized by FIG. 4, it was also predicted that the treatment of ADHD from a single 300 mg dose might produce an unacceptable incidence of side effects because the 300 mg dose could generate undesirable blood levels of modafinil. Thus the use of a split dose of 100 mg and 200 mg doses of modafinil administered in the manner described above was expected to provide the most favorable results, and particularly in the afternoon.

However, it has been surprisingly found that a single unit dose of modafinil containing between about 250 to about 350 mg of modafinil or between about 250 to about 450 mg, and in particular about 255, 300, 340 or 425 mg of modafinil, induces a beneficial neurological response with respect to the treatment of ADHD. Specifically, a single unit dose containing between about 250 to about 350 mg or between about 250 to about 450 mg, or between about 275 to about 325 mg or between about 325 to about 425 or about 255, 300, 340 or 425 mg of modafinil can be as effective as a 200 mg dose followed by a 100 mg dose or 200 mg dose, or a 100 mg dose followed by a 200 mg dose when the two doses are administered according to the split dose regimen described above, without the previously predicted incidence of undesirable side effects.

It has also been surprisingly found that the compositions of modafinil of the present invention provide significantly improved attention and significantly improved ADHD symptoms. The improvement in attention and ADHD symptoms was substantially the same as, and continued for a duration of time comparable to, both a) 100 mg of modafinil followed 4-6 hours later by 200 mg of modafinil, and b) 200 mg of modafinil followed 4-6 hours later by 100 mg of modafinil. Thus, a single dose of the present invention unexpectedly achieves improved attention and ADHD symptoms to a degree comparable to the double dosing regimen described hereinabove.

Figure 2:
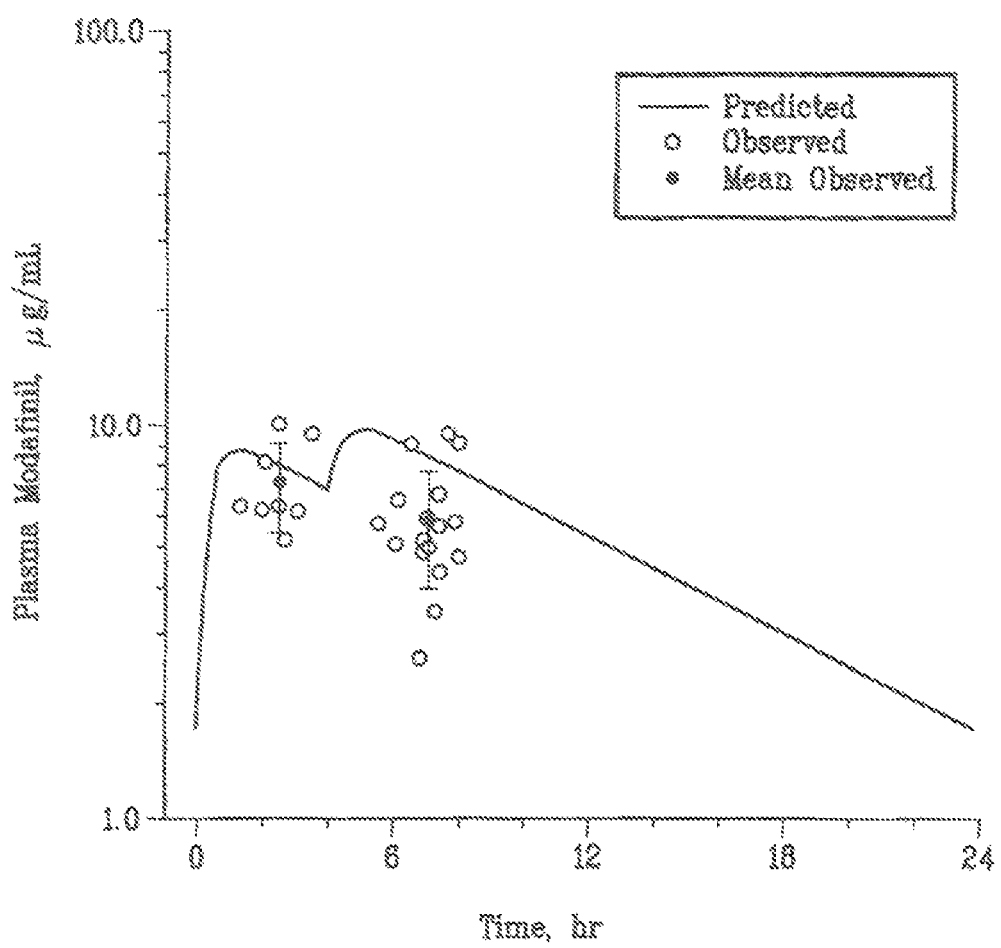
FIG. 2 represents a human blood plasma concentration curve of modafinil after an initial dose of 200 mg of modafinil followed 4 hours later by a 100 mg dose of modafinil.

As shown in FIGS. 1 and 2, the blood plasma concentration of modafinil begins to decrease after about two hours post administration of modafinil. In particular, FIGS. 1 and 2 show blood plasma concentrations of modafinil when a 100 mg dose is administered before (FIG. 1) or after (FIG. 2) a 200 mg dose is administered according to the regimen described above and in the brief description of FIGS. 1 and 2 above. FIGS. 1 and 2 also show that after blood levels of modafinil begin to decrease, the second dose of modafinil increases modafinil blood levels to a concentration that can be greater than the maximum blood levels achieved from the first dose.

Figure 3:
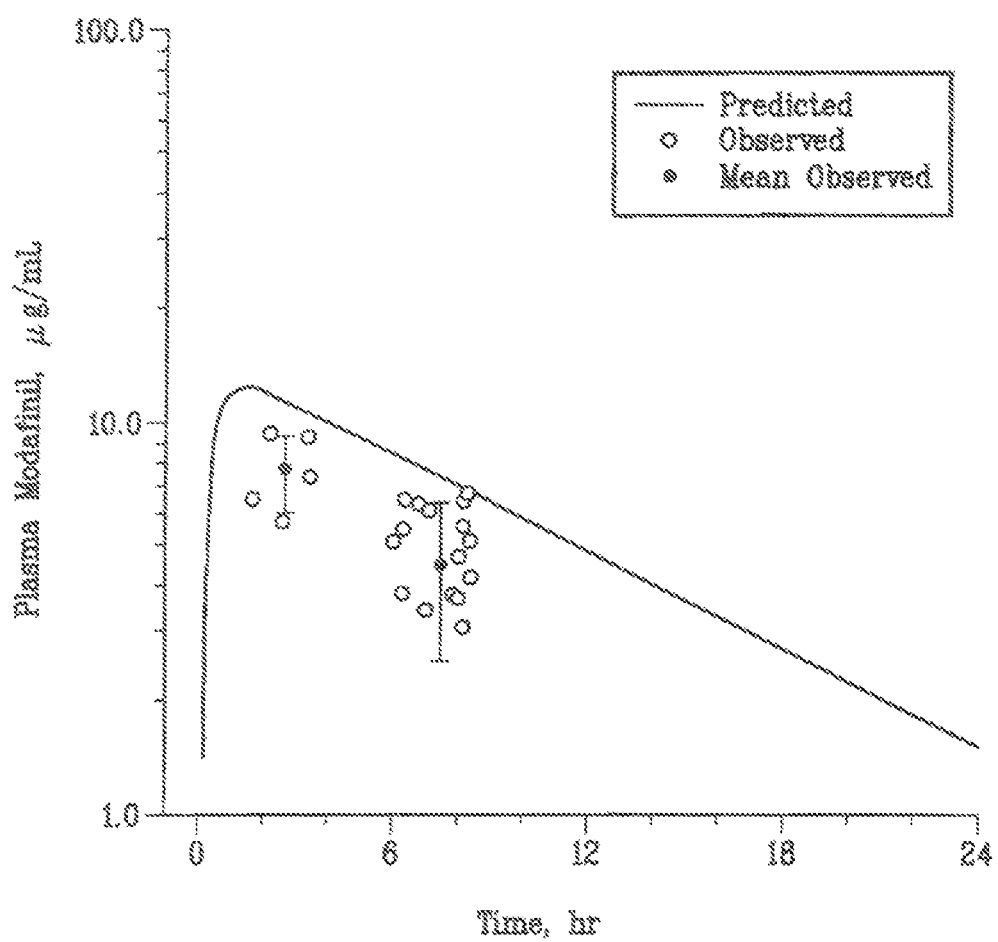
FIG. 3 represents a human blood plasma concentration curve of modafinil after a single dose of 300 mg of modafinil.

FIG. 3 provides the blood plasma concentration of modafinil after the administration of a single dose according to the present invention, namely 300 mg of modafinil. FIG. 3 shows that the blood level of modafinil also begins to decrease after about 2 hours post administration of the dose. From FIG. 3, it was also surprisingly found that the improved attention and improved ADHD symptoms resulted from blood concentrations of modafinil which were about 20-30% less than predicted, based upon an extrapolation of 100 mg unit dose data, and thus the predicted incidence of undesirable side effects can be avoided. Furthermore, it was concluded that the blood profile shown in FIG. 3 provides a desirable blood profile of modafinil blood concentration for the treatment of certain neurological conditions that are treatable by modafinil and described herein, such as ADHD. Accordingly, the present invention also includes a unit dose such that the oral administration of the unit dose to a human results in a blood profile of modafinil substantially as shown in FIG. 3.

Figure 5:
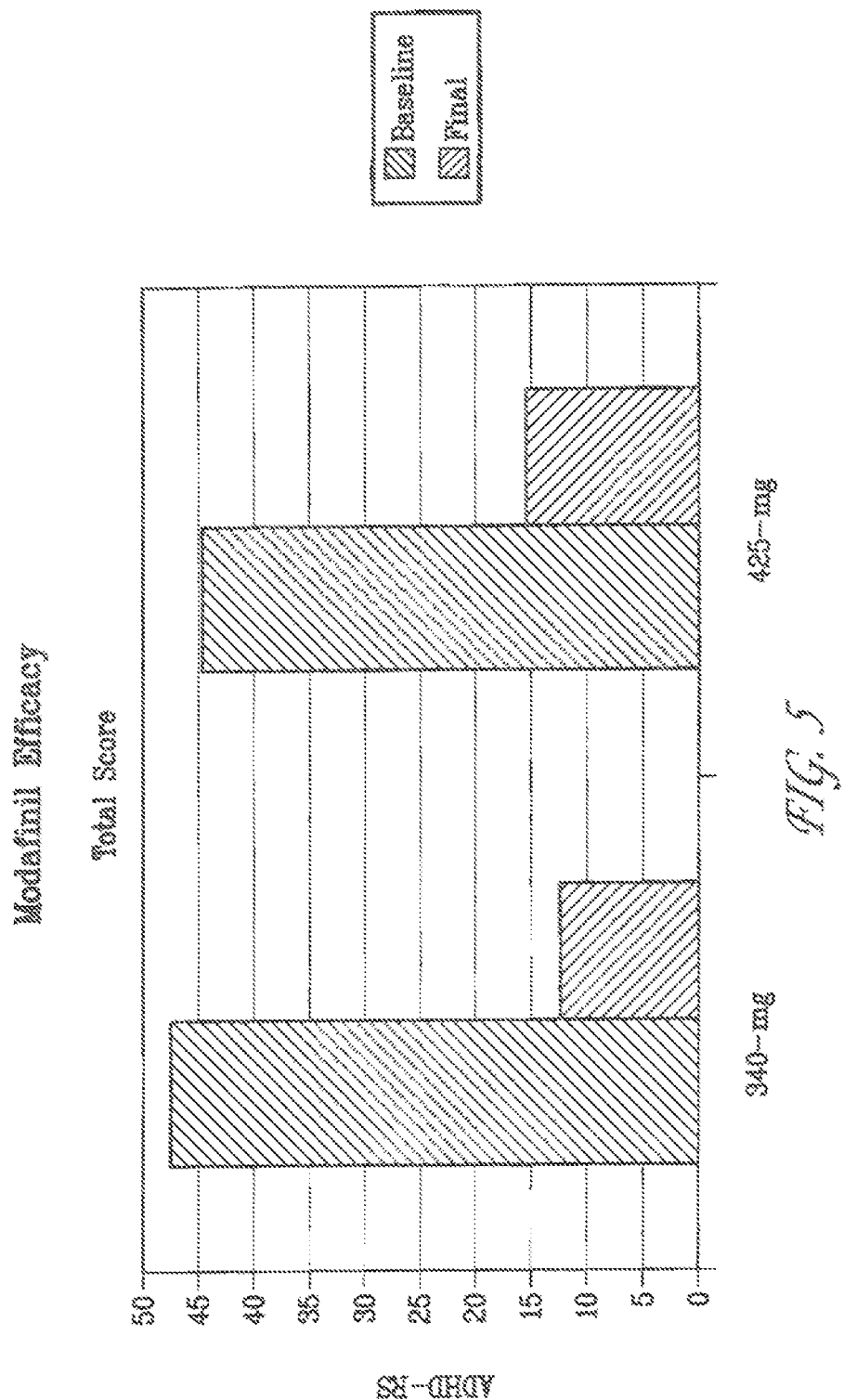
FIG. 5 represents a graph depicting the results of a clinical study showing the efficacy of 340 mg and 425 mg doses of modafinil in ADHD patients.

As shown in FIG. 5, significant and surprising improvements in ADHD were also obtained with single doses of 340 mg and 425 mg of modafinil.

Thus, the compositions and unit doses of the present invention can be beneficial to subjects in need of modafinil relative to conventional unit doses containing 100 mg and 200 mg of modafinil. Specifically, the present invention can increase the amount of time between required dosings of a subject and/or decrease the total number of doses of modafinil which may be required by a subject over a given period of time (e.g., in a 24 hour period or per day), i.e., a reduced need for split dose regimens.

2. The Composition of Modafinil of the Present Invention

As described above, the present invention provides pharmaceutical compositions containing between about 250 and about 350 mg of modafinil or between about 250 and about 450 mg of modafinil as well as compositions containing between about 275 and about 325 mg of modafinil, between about 325 and about 425 mg of modafinil or about 255, 300, 340 or 425 mg of modafinil. A pharmaceutical composition of the present invention can be a unit dose of modafinil, and in a preferred embodiment of the present invention a unit dose of modafinil, in tablet or capsule form including 250 to 350 mg of modafinil, 250 to 450 mg of modafinil, 275 to 325 mg of modafinil, 325 to 425 mg of modafinil, 255 mg of modafinil, 300 mg of modafinil, 340 mg of modafinil or 425 mg of modafinil.

In some embodiments, a unit dose of the invention can be prepared in a conventional manner, so as to maintain the relative proportions of modafinil and other pharmaceutical composition ingredients (e.g. lubricants and fillers) as compared to conventional 100 mg and 200 mg unit doses of modafinil. These embodiments are typically larger (in size and/or volume) than conventional 100 mg and 200 mg unit doses. Such unit doses of the present invention can also be prepared with or without one or more of magnesium silicate or talc.

In other embodiments of the present invention, the proportion of modafinil in the unit dose can be significantly higher than that of conventional 100 mg and 200 mg modafinil unit doses. The increase in weight percent of modafinil, while simultaneously reducing the weight percent of other ingredients, facilitates the manufacture of smaller (in size and/or volume) unit doses while still supplying the same amount of modafinil, i.e., 250 mg to 450 mg, to a subject. Such unit doses of the present invention can also be prepared with or without one or more of magnesium silicate or talc.

Typical embodiments include compositions of modafinil with one or more pharmaceutically acceptable excipients including but not limited to diluents, disintegrants, binders and lubricants. Preferably, the excipients meet the standards of the National Formulary ("NF") or United States Pharmacopoeia ("USP"). In a particular embodiment, there is provided a composition consisting of modafinil with one or more diluents, disintegrants, binders and lubricants.

In certain preferred embodiments, the composition comprises modafinil; one or more diluents, each independently chosen from a starch, a lactose monohydrate or a microcrystalline cellulose; one or more disintegrants, each independently chosen from a pregelatinized starch or a cross-linked sodium carboxymethyl cellulose; a binder; and a lubricant. In other preferred embodiments, the binder is a polyvinyl pyrrolidone, and the lubricant is magnesium stearate. In certain more preferred embodiments, a diluent is Fast Flo® #316, a second diluent is Avicel® PH 102; a disintegrant is Starch 1500®, a second disintegrant is Ac-Di-Sol®; and the binder is Povidone K-29/32. In other preferred embodiments, the diluent is Lactose Monohydrate, NF; the disintegrant is Croscarmellose Sodium, NF or Ac-Di-Sol®; and the binder is Povidone K90 D, USP. In other embodiments, the unit dose can be free of one or more of microcrystalline cellulose and pregelatinized starch.

In certain more preferred embodiments, the lactose monohydrate is Fast Flo® #316; the microcrystalline cellulose is Avicel® PH 102; the pregelatinized starch is Starch 1500®, the cross-linked sodium carboxymethyl cellulose is Ac-Di-Sol® and the polyvinyl pyrrolidone is Povidone K-29/32.

In one embodiment, modafinil is a substantial proportion of the composition by weight. In other embodiments, Fast Flo® #316 can be about 28.7%, the Avicel® PH 102 can be about 10.4%, the Starch 1500® can be about 10.9%, the Ac-Di- Sol® can be about 4.0%, the Povidone K-29/32 can be about 5.2% and the magnesium stearate can be about 0.8%.

In some embodiments, the total amount of modafinil present in the unit dose can be from about 45% to about 90% of the total unit dose weight. Preferably, the total amount of modafinil present in the unit dose can be about 60% to 80%, 85% to 90%, preferably 70% to 90%, 70% to 75%, most preferably 70% to 80% of the total unit dose weight.

In other embodiments, modafinil comprises from about 80-90% of the composition by weight. The composition can further include a diluent, such as a lactose monohydrate, preferably from about 3-15% of the composition by weight; a disintegrant, such as a cross-linked sodium carboxymethyl cellulose, preferably from about 2-10% of the composition by weight; a binder such as a polyvinyl pyrrolidone, preferably from about 2-10% of the composition by weight; and a lubricant such as magnesium stearate, preferably from about 0.2-2.0% of the composition by weight. In certain more preferred embodiments, the diluent is Lactose Monohydrate, NF, the disintegrant is Croscarmellose Sodium, NF, the binder is Povidone K90D, USP, and the lubricant is Magnesium Stearate, NF.

In one embodiment, modafinil is about 70% composition by weight. In the composition, Lactose Monohydrate, NF is about 20%, the Croscarmellose Sodium, NF about 4%, the Povidone, USP is about 5.2%, and the Magnesium Stearate, NF is about 0.8%.

In one embodiment, modafinil is about 75% composition by weight. In the composition, the Lactose Monohydrate, NF is about 15%, the Croscarmellose Sodium, NF is about 4%, the Povidone, USP is about 5.2%, and the Magnesium Stearate, NF is about 0.8%.

In another embodiment, modafinil is included in a composition of the present invention at about 80% of the composition by weight, the Lactose Monohydrate, NF is about 10%, the Croscarmellose Sodium, NF is about 4%, the Povidone K90 D, USP is about 5.2%, and the Magnesium Stearate, NF is about 0.8%. In a further embodiment, the Magnesium Stearate, NF is about 1%.

In yet another embodiment, the composition of the present invention includes modafinil at about 90% of the composition by weight, the Lactose Monohydrate, NF is about 3.5%, the Croscarmellose Sodium, NF is about 3%, the Povidone K90 D, USP is about 3%, and the Magnesium Stearate, NF is about 1%.

In embodiments where the modafinil is included in a unit dose such as a tablet, the tablet can include 300 mg of a modafinil in a 375 mg tablet (about 80% of the total tablet weight is attributed to modafinil). In other embodiments, the tablet can include 300 mg of modafinil in a 336 mg tablet (about 90% of the tablet weight is attributed modafinil). Similar calculations can be made for tablets containing between about 250 and 450 mg of modafinil.

Similarly, a capsule can contain 300 mg of a modafinil in a 375 mg capsule. A capsule can also contain 300 mg of modafinil in a 336 mg capsule. Similar calculations can be made for capsules containing between about 250 and 450 mg of modafinil.

Both the larger and smaller (higher weight percent of modafinil) size unit doses of the present invention, which include about 250 to 450 mg of modafinil, can exhibit the advantages over conventional unit doses as described above, such as enhanced treatment of ADHD and a reduction in the total number of doses of modafinil required per day by a subject, thereby enhancing patient compliance. However, the unit doses containing a higher percentage, by weight, of modafinil also can exhibit additional advantages, as described below.

First, patient compliance can increase because a unit dose of the present invention can be easier to swallow by subjects, in particular a solid unit dose form such as a tablet. Additionally, some of the unit doses of the present invention can facilitate administration of modafinil to pediatric subjects because the unit doses can contain a higher percentage, by weight, of modafinil and thus can have a smaller overall size and/or volume relative to the conventionally prepared unit doses containing 250 to 450 mg of modafinil.

When modafinil is administered in solid forms, the particle size of modafinil is preferably such that at least about 95% of the particles are less than about 200 μm in diameter. See, U.S. RE 37,516, the content of which is hereby incorporated by reference as though fully set forth herein.

In accordance with the present invention, the modafinil can also be formulated in liquid forms and administered in multiple ways, e.g., by spoon, mixed with foods or drinks, capsules, etc. Liquid unit doses of modafinil are described in U.S. RE 37,516, and other alternative dosage forms are described in U.S. Patent Pub. Nos.: 02-0099097 and 02-0098240 and PCT Publication No. 02/056915, the contents of which are hereby incorporated by reference as though fully set forth herein.

3. Examples

Example 1

A group of 248 children (average age: 9 years, average weight: 35.5 kilograms) were studied to determine the effect of modafinil on ADHD.

After a 1 week washout period, children with moderate to severe ADHD received 4 weeks of treatment with placebo or modafinil in split morning/midday dosages of 100/200 mg, 200/100 mg, a single 300 mg dose, and 200/200 mg (400 mg total). Randomization called for equal distribution of the children by weight, except for the 200/200 mg dose group, which contained only children having a weight greater than or equal to 30 kg. The primary efficacy measure was the teacher rated ADHD Rating Scale-IV.

Results indicated that modafinil significantly improved ADHD symptoms for the primary outcome measure for the 200/100 mg and 300 mg once daily dose. The results of the study also indicated that modafinil was safe and generally well tolerated, however, studies have also revealed that 400 mg of modafinil has a higher adverse event profile than the other doses.

Example 2

Safety and efficacy of the fixed doses of 340-mg and 425-mg were evaluated following a 2-week dosing period (1-week of titration and 1-week at steady state). The 340-mg dose was administered to children weighing <30 kg, and the 425-mg dose was administered to children weighing ≥30 kg.

The 24 children enrolled in this study were predominately male (17M:7F) and predominately white (13W:9B:2Other). The average age (9.0 yrs), weight (32.9 kg) and height (133.7 cm) were similar to those seen in previous ADHD trials in children. The children <30 and ≥30 kg were approximately equaled divided. The average Attention Deficit Hyperactivity Disorder Rating Scale (ADHD-RS) total score at baseline was 46.3.

Following 2-weeks of treatment with either 340 mg or 425 mg modafinil, single dose per day, the baseline ADHD-RS total scores (46.3) decreased significantly, representing approximately a 70% improvement from baseline. This data is represented in FIG. 5.

Example 3

Formulations

| Excipients | Amount per 255 mg tablet (mg) | Amount per 340 mg tablet (mg) | Amount per 425 mg tablet (mg) |
|---|---|---|---|
| Modafinil drug substance | 255.0 | 340.0 | 425.0 |
| Lactose, NF | 51.0 | 68.0 | 85.0 |
| Povidone USP | 17.7 | 23.6 | 29.5 |
| Croscarmellose Sodium, NF | 13.5 | 18.0 | 22.5 |
| Purified Water, USP | q.s. | q.s. | q.s. |
| Magnesium Stearate, NF | 2.7 | 3.6 | 4.5 |
| Total Tablet Weight | 339.9 | 453.2 | 566.5 |

Although the present invention has been described in considerable detail, those skilled in the art will appreciate that numerous changes and modifications may be made to the embodiments and preferred embodiments of the invention and that such changes and modifications are within the scope of the present invention. Additionally, each reference cited herein is hereby incorporated by reference.

What is claimed is:

1. A method of treating ADHD in a pediatric subject, comprising the step of administering to the subject a unit dose containing about 250 to about 450 mg of modafinil, wherein the tablet is free of magnesium silicate and talc, and wherein the unit dose is a tablet and about 70-90% of the tablet weight is modafinil.

2. The method of claim 1, wherein the modafinil is R-(−) 2-[(diphenylmethyl)sulfinyl] acetamide.

3. The method of claim 1, wherein the unit dose contains about 275 to about 325 mg of modafinil.

4. The method of claim 1, wherein the unit dose contains about 325 to about 450 mg of modafinil.

5. The method of claim 1, wherein the unit dose contains about 255 mg of modafinil.

6. The method of claim 1, wherein the unit dose contains about 340 mg of modafinil.

7. The method of claim 1, wherein the unit dose contains about 425 mg of modafinil.

8. The method of claim 1, wherein about 70-75% of the tablet weight is modafinil.

9. The method of claim 1, wherein about 80% of the tablet weight is modafinil.

10. The method of claim 9, wherein the modafinil is R-(−) 2-[(diphenylmethyl)sulfinyl] acetamide.

* * * * *